US00PP34542P2

(12) United States Plant Patent
Krebs

(10) Patent No.: US PP34,542 P2
(45) Date of Patent: Sep. 6, 2022

(54) ***RHODODENDRON* PLANT NAMED 'HOLDENRHODO214'**

(50) Latin Name: *Rhododendron hybrida*
Varietal Denomination: 'HoldenRhodo214'

(71) Applicant: Stephen Krebs, Painesville, OH (US)

(72) Inventor: Stephen Krebs, Painesville, OH (US)

(73) Assignee: Holden Forests and Gardens, Kirtland, OH (US)

( * ) Notice: Subject to any disclaimer, the term of this patent is extended or adjusted under 35 U.S.C. 154(b) by 0 days.

(21) Appl. No.: 17/550,555

(22) Filed: Dec. 14, 2021

(51) Int. Cl.
*A01H 5/02* (2018.01)
*A01H 6/36* (2018.01)

(52) U.S. Cl.
USPC ..... Plt./239
CPC ..... *A01H 6/364* (2018.05)

(58) Field of Classification Search
USPC ..... Plt./239, 240
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Rhododendron* plant named 'HoldenRhodo214' is disclosed, characterized by showy rose-purple flowers, and dark, glossy foliage 'HoldenRhodo214' has a compact habit and has been observed to have a high survival rate in evaluation fields known to contain the root rot soil pathogen *Phytophthora cinnamomi*. Also observed is robust growth in full sun in unamended sand and gravel loam soils, up to pH 6.2. Profuse and consistent flowering, with plant and flower buds hardy to at least −26° C. The new variety is a *Rhododendron*, typically produced as an outdoor ornamental plant.

2 Drawing Sheets

Figure 1:
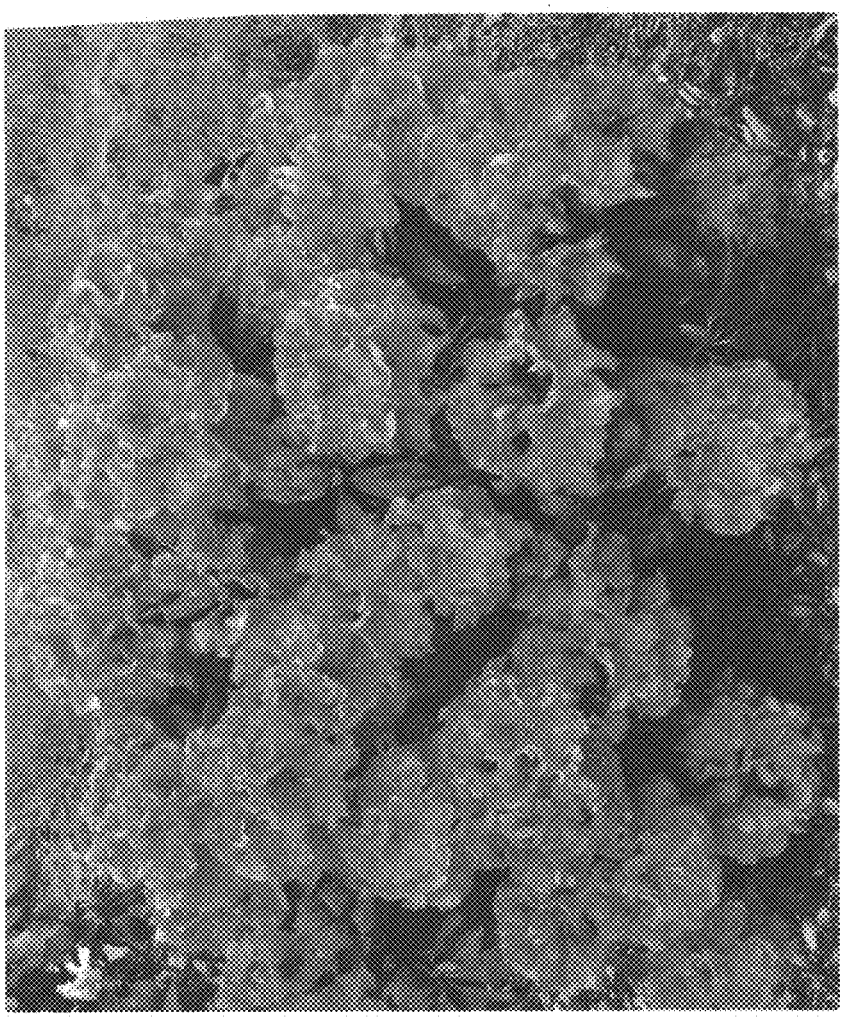

Latin name of the genus and species: *Rhododendron hybrida.*

Variety denomination: 'HoldenRhodo214'.

BACKGROUND OF THE INVENTION

The new cultivar is a product of a planned breeding program by the inventor. *Rhododendron* 'HoldenRhodo214' is the result of a crossing of the unpatented *Rhododendron* 'Ingrid Mehlquist' as the seed parent with the pollen parent *Rhododendron* 'Rio', unpatented. The crossing resulting in the new variety was made during the Spring of 2000.

The new variety was selected as a seedling, resulting from the crossing made during the Spring of 2000 by the inventor in the Spring of 2007 at a research nursey in Madison, Ohio. After identifying the new variety as a potentially interesting selection, the inventor continued confidential trial growing of 'HoldenRhodo214' to assess the stability of characteristics unique to this variety.

Asexual reproduction of the new cultivar 'HoldenRhodo214' was first performed during the Autumn of 2007 at the same nursery in Madison, Ohio by vegetative cuttings. Through subsequent propagation, multiple additional generations have been reproduced, having shown that the unique features of this cultivar are stable and reproduced true to type.

SUMMARY OF THE INVENTION

The cultivar 'HoldenRhodo214' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of HoldenRhodo214'. These characteristics in combination distinguish 'HoldenRhodo214' as a new and distinct *Rhododendron* cultivar:

1. Showy, rose-purple flowers with strong marginal undulation, ie: ruffling.
2. Profuse and consistent flowering, with plant and flower buds hardy to at least −15° F./−26° C.
3. Compact habit with dark, glossy foliage.
4. Robust growth in full sun in unamended sand and gravel loam soils, up to pH 6.2.
5. High survival in evaluation fields known to contain the root rot soil pathogen *Phytophthora cinnamomi.*

PARENT COMPARISON

Plants of the new cultivar *Rhododendron* 'HoldenRhodo214' are similar to the seed parent, in most horticultural characteristics. The new variety, however, differs in the following:

1. Inflorescence size of the new variety is about 2 times larger than the seed parent.
2. Flare on the flowers is more pronounced on the new variety than the seed parent.
3. Flower color of the new variety is a non-fading rose-purple, compared to the pink flowers of the seed parent that fade to white.

Plants of the new cultivar *Rhododendron* 'HoldenRhodo214' are similar to the pollen parent in most horticultural characteristics. The new variety, however, differs in the following:

1. Growth habit of the new variety is much more compact than the pollen parent, with smaller, glossier foliage.

2. The new variety's resistance to root rot is greater than the pollen parent.
3. Flowers of the new variety are strongly pigmented rose-purple in color, compared to the pale pink flowers with yellow highlights of the pollen parent.

COMMERCIAL COMPARISON

*Rhododendron* 'HoldenRhodo214' can be compared to compared to the commercial variety *Rhododendron* 'Besse Howells', unpatented. Plants of 'HoldenRhodo214' are similar to plants of 'Besse Howells' in most horticultural characteristics, however, plants of 'HoldenRhodo214' differ in the following:

1. The new variety has a much more compact growth habit than this comparator.
2. Foliage of the new variety is darker green, smaller, and glossier than this comparator.
3. This comparator is more susceptible to root rot disease than the new variety.

'HoldenRhodo214' can be compared to the commercial variety *Rhododendron* 'Mardi Gras', unpatented. Plants of 'HoldenRhodo214' are similar to plants of 'Mardi Gras' in most horticultural characteristics, however, plants of 'HoldenRhodo214' differ in the following:

1. Flower bud cold hardiness of 'HoldenRhodo214' is at least USDA Hardiness Zone 5, compared to Zone 6 for this comparator.
2. Flowers of the new variety are rose-purple and are more strongly and evenly pigmented than the rose-pink and white bicolor flowers of this comparator.
3. The new variety lacks conspicuous leaf hairs present on this comparator.

BRIEF DESCRIPTION OF THE PHOTOGRAPHS

The accompanying photograph in FIG. 1 illustrates in full color a typical plant of 'HoldenRhodo214' grown outdoors in Madison, Ohio. This plant is approximately 10 years old, grown in the ground.

Figure 2:
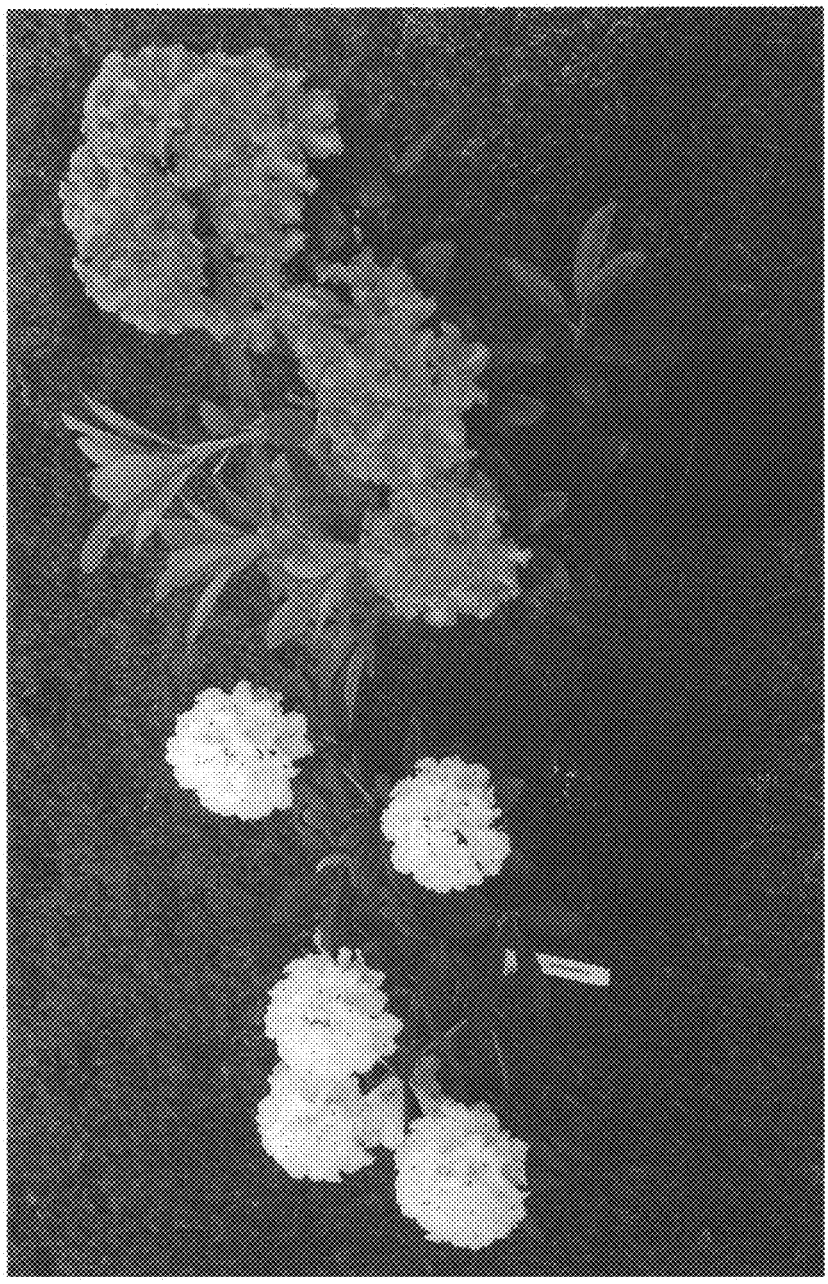

FIG. 2 illustrates in full color a 3-year old plant of 'HoldenRhodo214'(right) and the seed parent 'Ingrid Mehlquist'(left).

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'HoldenRhodo214' plants grown outdoors in Madison, Ohio. No artificial light, photoperiodic treatments were given to the plants. Measurements and numerical values represent averages of typical plant types.

Botanical classification: *Rhododendron* 'HoldenRhodo214'.

PROPAGATION

Root initiation: Roots from semi-hardwood cuttings taken in late Summer or Autumn. Stem cuttings are wounded and dipped in 7500 ppm IBA for 5s.

Root description: Fibrous, white aging to brown. Color not accurately measured with RHS Chart.

PLANT

General growing conditions: Open-field conditions during Spring in Northeast Ohio, unamended gravel loam soil, pH 6.2.

Growth habit: Compact and densely branched.

Height: 83 cm.

Plant spread: Approximately 116 cm in length, 91 cm in width.

Age of plant described: Approximately 10 years.

Growth rate: Moderate.

Branching characteristics: Well-branched, dense.

Primary branches:

*Quantity.*—3 to 5.

*Length.*—About 8 to 12 cm, then splitting to lateral branches.

*Diameter.*—About 2.5 cm.

*Strength.*—Very strong.

*Texture.*—Young: Glabrous. Mature: Coarsely striated.

*Color.*—Young: Near RHS Yellow-Green 144A. Mature: Near RHS Greyed-Orange 177A with coarse striation colored near Grey-Brown 199A.

Length of lateral branches: 58 cm.

Number of lateral branches: Approximately 11.

Diameter of lateral branches: 2 cm.

Angle of attachment: 45°.

Pinching required: Minimal.

Lateral branch shape: Cylindrical/conical.

Lateral branch strength: Strong.

Lateral branch color: Mature: Combination of colors near RHS Grey-Brown 199A, Greyed-Green 198D, and Greyed-Orange 177B. Young: Near RHS Yellow-Green N144C.

Internode: 1 to 3 cm.

FOLIAGE

Leaf:

*Arrangement.*—Alternate.

*Shape.*—Elliptic to oblanceolate.

*Average length.*—7.7 cm.

*Average width.*—3.4 cm.

*Apex.*—Broadly acute.

*Base.*—Broadly cuneate to rounded.

*Margin.*—Entire.

*Texture of top surface.*—Glabrous.

*Texture of bottom surface.*—Glabrous.

*Color.*—Young foliage upper side: Near RHS Green 143B. Young foliage under side: Near RHS Green 143C. Mature foliage upper side: Near RHS Yellow-Green 147A. Mature foliage under side: Near RHS Yellow-Green 146C.

Venation:

*Type.*—Pinnate.

*Color, upper side.*—Near RHS Yellow-Green 153C.

*Color, under side.*—Near RHS Yellow-Green 154D.

Petiole:

*Length.*—1 cm.

*Width.*—0.6 cm.

*Color, upper surface.*—Near RHS Yellow-Green 151A.

*Color, lower surface.*—Near RHS Yellow-Green 151D.

*Texture.*—Glabrous.

FLOWER

Natural flowering season: May in Northeast Ohio.
Inflorescence:
*Arrangement.*—Terminal buds open to clusters of single, perfect, broadly funnel-shaped flowers.
*Type.*—Raceme.
*Height.*—11 cm.
*Width.*—13 cm.
*Quantity of flowers.*—About 13 to 16 flowers per inflorescence.
*Typical quantity of inflorescences per plant.*—90 to 110.
Bud:
*Shape.*—Elliptic.
*Length.*—2.8 cm.
*Diameter.*—1.5 cm.
*Color.*—Near RHS Red-Purple 61B.
Flower:
*Shape.*—Campanulate.
*Facing direction.*—Outward.
*Quantity per lateral stem.*—1 inflorescence per terminal shoot.
*Diameter of entire flower.*—6.5 cm.
*Depth/length.*—7.3 cm.
*Rate of opening.*—Approximately 100% of flowers open at once on whole plant.
*Longevity on plant.*—Individual flowers 7 days; total duration of bloom ranges from 2 to 3 weeks, weather depending.
*Persistent or self-cleaning.*—Self-cleaning.
*Fragrance.*—None detected.
Tube:
*Length.*—3.8 cm.
*Width.*—At widest point: 2.2 cm. At narrowest point: 0.4 cm.
Petals: Measurements for unfused petal segments.
*Number.*—5.
*Margin.*—Entire, strongly undulating, ruffled.
*Apex.*—Rounded and undulating.
*Length.*—Approximately 2.6 cm.
*Width.*—Approximately 3.6 cm.
*Shape.*—Orbicular to semi-circular.
*Fused.*—Partially, approximately 45% of their length.
*Texture.*—Glabrous.
*Color.*—First opening: Interior Surface: Near RHS Red-Purple 64C. Dorsal petal has linear speckles near RHS Dark Red 183B. Exterior Surface: Near RHS Red-Purple 60D. Mature: Interior Surface: Near RHS Red-Purple N66D. Dorsal petal has linear speckles near RHS Greyed-Purple 183C. Exterior Surface: Near RHS Red-Purple 67B. Fading: Interior Surface: Near RHS Red-Purple N57C. Dorsal petal has linear speckles near RHS Red-Purple 59A. Exterior Surface: Near RHS Red-Purple 73A.
Sepal/calyx:
*Quantity.*—5, highly reduced.
*Margin.*—Entire.
*Shape.*—Narrowly deltate.
*Length.*—0.2 cm.
*Width.*—0.3 cm.
*Apex.*—Rounded.
*Base.*—Fused.
*Texture.*—Glabrous.
*Color.*—Inner Surface: RHS Green 143C. Outer Surface: RHS Green 143C.
Peduncles:
*Length.*—2 cm.
*Diameter.*—0.8 cm.
*Angle.*—Vertical.
*Strength.*—Strong attachment to terminal shoot.
*Color.*—Near RHS Yellow-Green 144C.
*Texture.*—Glabrous.
Pedicel:
*Length.*—3 cm.
*Width.*—0.2 cm.
*Angle.*—45-70° from peduncle.
*Strength.*—Moderately strong.
*Texture.*—Glabrous.
*Color.*—Near RHS Yellow-Green 145A.

REPRODUCTIVE ORGANS

Stamens:
*Number.*—10.
*Length.*—Approximately 2.2 cm.
*Width.*—Approximately 0.1 cm.
Anthers:
*Length.*—Approximately 0.3 cm.
*Color.*—Near RHS Greyed-Orange 175A.
*Pollen.*—Some, appears to be sterile.
Pistil:
*Number.*—1 per flower.
*Length.*—3.6 cm.
Stigma:
*Shape.*—Round.
*Color.*—Near RHS Greyed-Orange 166C.
*Style length.*—3.3 cm.
*Style color.*—Near RHS White 155C.
*Ovary color.*—Near RHS Green 143C.

OTHER CHARACTERISTICS

Disease resistance: Field resistance to root rot caused by *Phytophthora cinnamomic*. Neither resistance nor susceptibility to other diseases has been observed. Neither resistance nor susceptibility to normal diseases and pests of *Rhodendendron* has been observed.
Drought tolerance and cold tolerance: Not measured.
Fruit/seed production: Appears to be sterile. No open pollinated seed produced, and crosses in either direction yield no seeds.

What is claimed is:

1. A new and distinct cultivar of *Rhododendron* plant named 'HoldenRhodo214' as herein illustrated and described.

* * * * *